(12) United States Patent
Mark

(10) Patent No.: US 6,238,120 B1
(45) Date of Patent: May 29, 2001

(54) FLUID APPLICATOR

(76) Inventor: Phillip E. Mark, 6417 Marlberry Dr., Orlando, FL (US) 32819

( * ) Notice: Subject to any disclaimer, the term of this patent is extended or adjusted under 35 U.S.C. 154(b) by 0 days.

(21) Appl. No.: 09/545,510

(22) Filed: Apr. 7, 2000

(51) Int. Cl.⁷ ...................................................... B43K 1/06
(52) U.S. Cl. ........................ 401/265; 401/282; 401/286; 401/183; 401/134; 604/310
(58) Field of Search ..................... 401/203, 183, 401/184, 185, 261, 265, 266, 119, 123, 129, 282, 286, 289, 134; 604/2, 3, 310

(56) References Cited

U.S. PATENT DOCUMENTS

| | | | |
|---|---|---|---|
| 226,500 | * | 4/1880 | Davids ................................. 401/119 |
| 1,173,194 | * | 2/1916 | Kohl et al. ............................ 401/282 |
| 1,578,449 | * | 3/1926 | Leraas .................................. 401/286 |
| 2,090,354 | * | 8/1937 | Massman ............................. 401/119 |
| 3,359,992 | | 12/1967 | Cishek et al. . |
| 3,499,686 | | 3/1970 | Landen et al. . |
| 3,723,015 | * | 3/1973 | Wissler et al. ....................... 401/286 |
| 3,938,898 | | 2/1976 | Reitknecht . |
| 4,222,677 | | 9/1980 | Cervantes . |
| 4,498,796 | * | 2/1985 | Gordon et al. ....................... 401/134 |
| 4,578,055 | | 3/1986 | Fischer . |
| 4,619,613 | | 10/1986 | Dragan . |
| 4,963,093 | | 10/1990 | Dragan . |
| 4,997,371 | | 3/1991 | Fischer . |
| 5,052,927 | | 10/1991 | Discko, Jr. . |
| 5,083,921 | | 1/1992 | Dragan . |
| 5,122,057 | | 6/1992 | Discko, Jr. . |
| 5,129,825 | | 7/1992 | Discko, Jr. . |
| 5,165,890 | | 11/1992 | Discko, Jr. . |
| 5,246,371 | | 9/1993 | Fischer . |
| 5,267,859 | | 12/1993 | Discko, Jr. . |
| 5,269,684 | | 12/1993 | Fischer . |
| 5,286,257 | | 2/1994 | Fischer . |
| 5,324,273 | | 6/1994 | Discko, Jr. . |
| 5,336,088 | | 8/1994 | Discko, Jr. . |
| 5,570,966 | | 11/1996 | Phelan . |
| 5,816,804 | | 10/1998 | Fischer . |

* cited by examiner

Primary Examiner—David J. Walczak
(74) Attorney, Agent, or Firm—Eric P. Schellin

(57) ABSTRACT

A fluid applicator system having a proximal end portion that has a male portion that can be connected to a female inner threaded hub that in turn is attached to a source of a fluid supply. The distal end terminates in a ball that is flocked with bristles that are adhered perpendicularly to the ball. The proximal end and the distal end is fluidly connected by a series of cylindrical tubes that are of decreasing outer diameter from the proximal end in the direction of the distal end.

2 Claims, 3 Drawing Sheets

FLUID APPLICATOR

BACKGROUND OF THE INVENTION

Increasingly there is a need for tiny fluid applicators to distribute relatively small quantities of a fluid from a source to the site where it is needed.

Such small applicators have found ready acceptance in dentistry where small quantities of liquid medicament must be applied to the interstices of teeth. Such small applicators are also used by hobbyists to supply a liquid adhesive to parts that are assembled. Such small applicators are useful in applying small quantities of fluid lubricants to watch parts in the horology industry or small mechanical movements in the auto industry. The fluid applicators are also used for cosmetic purposes.

In all of such uses a small fluid containing source or reservoir is fluidly and operatively aligned with a small applicator usually of the disposable kind.

SUMMARY OF THE INVENTION

The invention is concerned with a fluid applicator system having a proximal end portion that has a threaded male portion that can be fluidly connected to a female inner threaded hub that in turn is attached to a source of a fluid. The distal end terminates in a ball that has a conduit therethrough. The ball is flocked with bristles that are adhered perpendicularly to the surface of the ball. The proximal end and the distal end is fluidly connected by a series of cylindrical tubes that are stepped with decreasing outer diameter from the proximal end in the direction of the distal end.

DETAILED DESCRIPTION OF THE PREFERRED EMBODIMENTS

Figure 1:
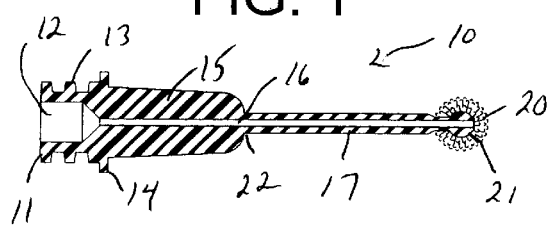
FIG. 1 is a cross-sectional view of the applicator of the present invention.
Figure 2:
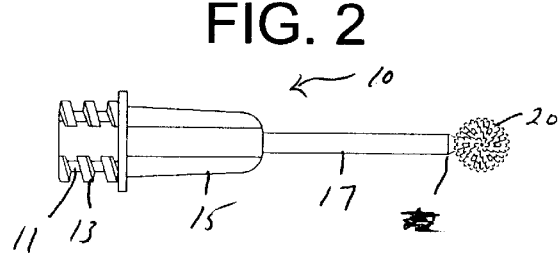
FIG. 2 is a perspective of the applicator of the present invention.

Attention is directed to FIGS. 1 and 2 for the general structure 10 of the fluid applicator of the present invention. FIG. 1 is in cross-section while FIG. 2 depicts a perspective view of the device. The proximal portion 11 has a short relatively large diameter internal bore 12 and has a screw threaded portion 13. The threaded portion 13 terminates in an abutment flange 14 which extends outwardly radially. On the other side of the flange 14 is cylindrical first tubular portion 15. A relatively smaller diameter bore 16 extends therethrough being fluidly connected at one end to the bore 12 of the proximal portion 11. The cylindrical portion 15 has cylindrical second tubular extension 17 of lesser diameter than cylindrical portion 15. The bore 16 continues through the cylindrical extension 17. The cylindrical extension 17 terminates in still another third tubular extension 30 to which a flocked ball 20 may be attached at its distal end 21. The bore 16 continues through the still another extension 30. Any fluid charged through bore 16 emanates through the flocked ball 20 for dispensing. The confluence of cylindrical portion 15 and cylindrical extension 17 in one embodiment may have a weakened portion 22 which provides a fulcrum about which extension 17 may be angled.

Figure 3:
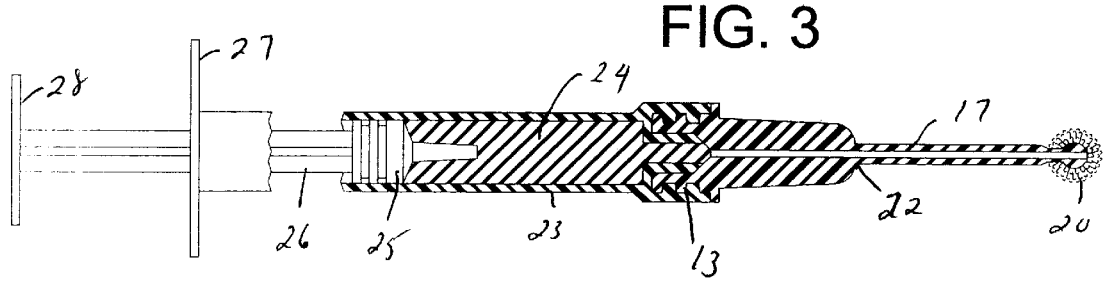
FIG. 3 is similar to FIG. 1 having a fluid containing syringe attached thereto.

In FIG. 3 one can see the applicator of the present invention which has mounted about the threaded portion 13 a syringe 23 shown in partial cross-section and fragmentary, which has therein a fluid content 24. The syringe 23 has a piston 25 to which is attached a piston rod 26. The syringe has conventional radially extending finger abutment 27 and the piston rod 26 terminates at its proximal end with conventional radially extending finger abutments 28.

Figure 4:
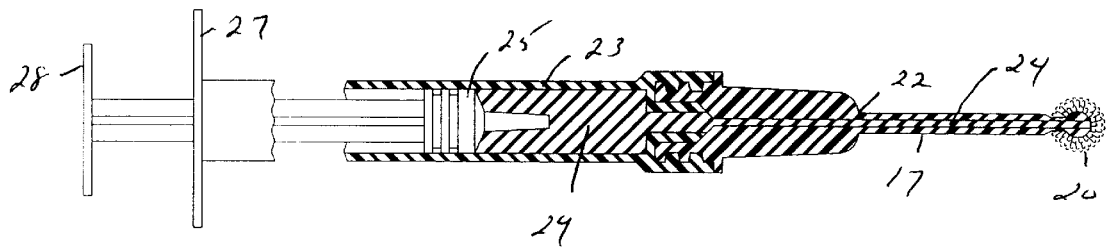
FIG. 4 is similar to FIG. 3 showing the syringe in an expelling condition forcing liquid from the applicator.

In FIG. 4 the syringe piston 25 has been driven whereby to drive the fluid 24 through bore 16 in the direction of the distally positioned flocked ball 20 for distribution therethrough.

Figure 5:
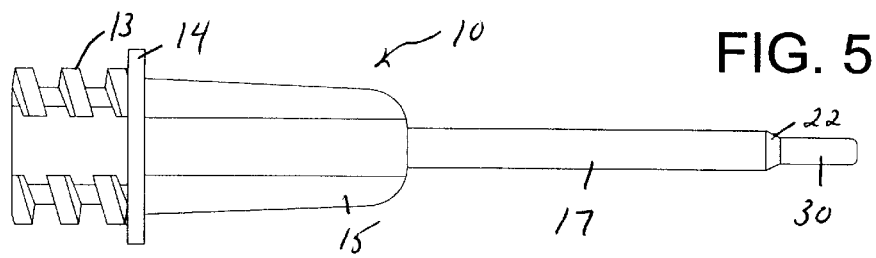
FIG. 5 is a perspective of the applicator without the applicable flocked ball.

In FIG. 5, the applicator 10 of the present invention terminates in a relatively small tube 30. This arrangement is desirable when no flocked ball is necessary that is when fluid is dispensed in droplet form or is dispensed by direct contact for simple fluid flow.

Figure 6:
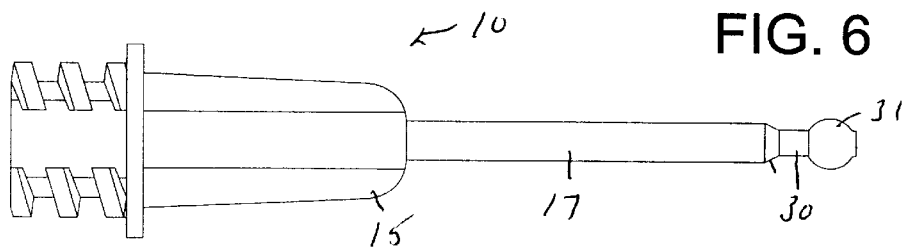
FIG. 6 is similar to FIG. 5 with the applicator ball shown schematically.

In FIG. 6, the applicator of the present invention is depicted similarly as in FIG. 5. However, note that tube 30 terminates in a ball 31 having a bore 32 therethrough.

Figure 7:
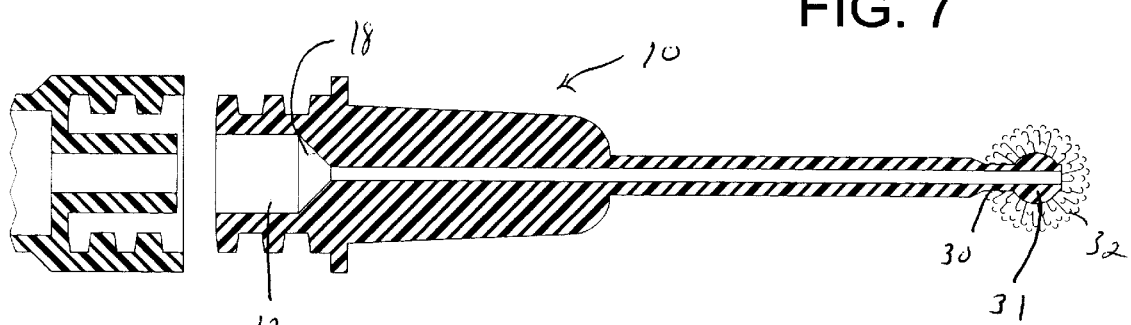
FIG. 7 is a cross section view similar to FIG. 1 with female portion of the syringe exploded from the applicator.

FIG. 7 is similar to FIG. 3 but is enlarged and gives a cross-sectional and fragmentary view of the distal end of the syringe and cross-sectional view of the applicator 10. The ball 31 is shown as being flocked with bristles 32. Note that the bore 12 terminates in a sloped or tapered portion 18 at its base.

The bristles are affixed by an adhesive which may be affixed by electrostatic assisted alignment as taught by a number of patents.

Figure 8:
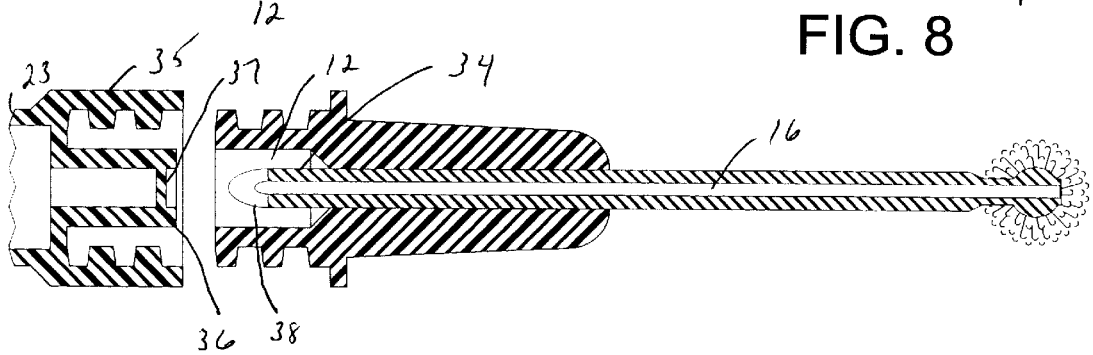
FIG. 8 is similar to FIG. 7 but depicts a second embodiment wherein the applicator has a centrally located spike for penetration through a membrane of a container of fluid.

FIG. 8 is to another embodiment and is a modification of the embodiment shown in FIG. 7. The bore 12 is provided with an outwardly directed tubular spike 34 which is concentric with bore 12 and is in fluid connection with bore 16. The connecting distal female internally threaded member 35 has a tube 36 which connects with the main portion of the syringe 23 or fluid containing reservoir. The tube 36 terminates in a diaphram membrane 37 into which the bevelled point 38 may be penetrated. The resultant is illustrated in fragmentary cross-sectional view of FIG. 9. The fluid contents in the syringe or the fluid containing reservoir is then ejected to flow through conduit 16 for egress from the flocked bristled ball 32. When a spike arrangement is employed as in FIGS. 8 and 9 the spike and tube may be constructed of a metal.

Figure 10:
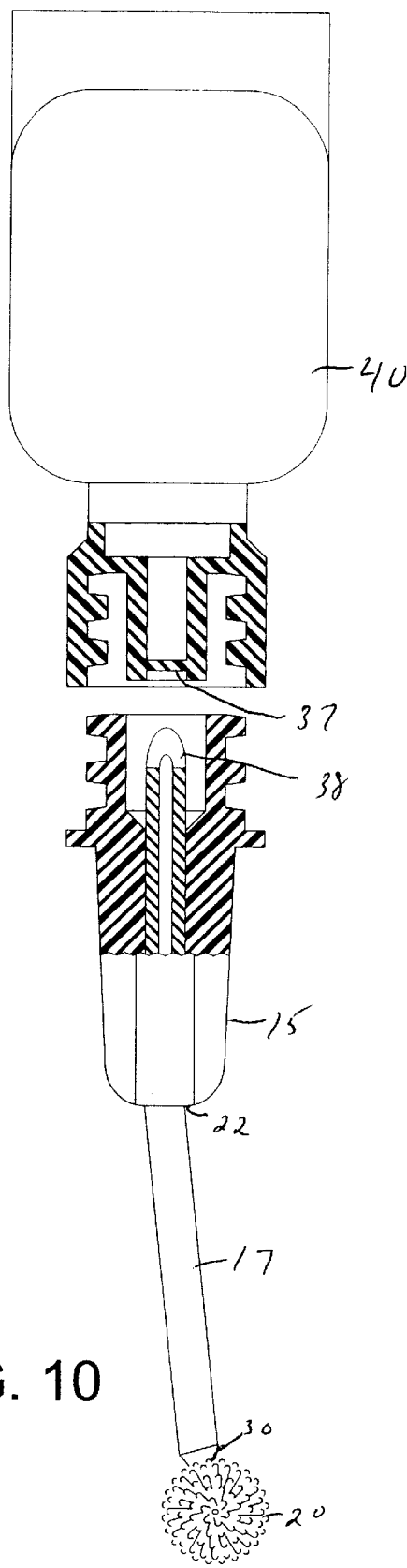
FIG. 10 is a partial cross-sectional view of another embodiment of the applicator of the present invention.

FIG. 10 illustrates a further embodiment in partial cross-section and is detailed to show the present invention with a fluid containing reservoir 40 which has a threaded female hub 35 affixed to the reservoir 40 for attachment to the applicator. The embodiment shown by FIG. 10 illustrates an acute bend at the juncture of cylindrical extension 17 that is, at the weakened portion 22.

In another embodiment, it is contemplated that the extension 17 and another extension 30 may be constructed of an elongated metal tube.

Figure 11:
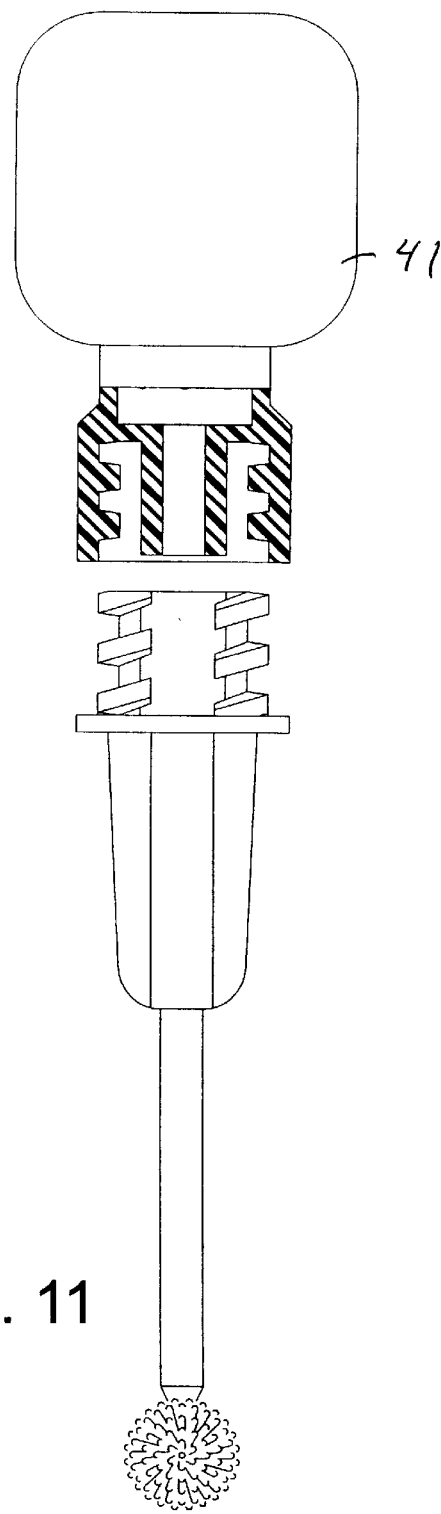
FIG. 11 is yet to another embodiment of the present invention.

FIG. 11, depicts another utility of the liquid applicator of the present invention. Instead of a syringe or instead of fluid containing reservoir, the internally threaded hub 35 is fitted with a bulb 41 which may be employed to aspirate fluid from an appropriate source. In operation, the bulb 41 is manually squeezed to collapse it. The tip of the applicator is dipped into a quantity of liquid. The bulb 41 is freed whereby it resumes its normal configuration and thereby sucks liquid up into the applicator. The liquid may be then distributed in much in the manner of an eye dropper.

The bulb 41 and the hub 35 may be blow molded as an integral unit. On the other hand the bulb may be of rubber which is fitted to the hub 35.

The hub 35 and the applicator have been illustrated as being connectable by male and female attachment means which is the preferred arrangement. Other means may be utilized such as a friction fit or a bayonet connection, however, these alternative arrangements may not be sufficiently liquid tight or may become disengaged during the application of fluid.

Figure 9:
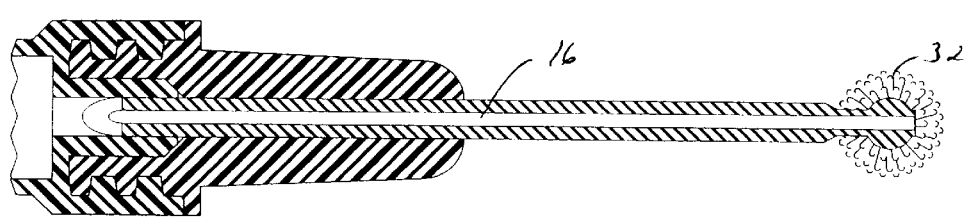
FIG. 9 is similar to FIG. 8 depicting the spike of the applicator in fluid connection to the container of fluid.

The materials of construction may be any of numerous thermosetting or thermoplastic resins concentrically available except in the alternative embodiment where metal conduits are utilized and displayed in FIGS. 8 and 9. In FIG. 11, for instance cylindrical 17 may be of metal as a blend is to be achieved, although not necessary if a resinous material is employed and there is a weakened portion 22 where a convenient bend may be achieved.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A fluid applicator system comprising a proximal male threaded portion, said male threaded portion having a relatively large cavity, an elongated cylindrical first tube downstream from said male threaded portion and having a relatively smaller bore than said cavity in fluid connection with said cavity, an elongated cylindrical second tube extending further downstream directly from said first tube, said second tube having a bore in alignment and in fluid connection with the bore in said first tube, the outer diameter of said second tube being relatively smaller than the outer diameter of said first tube, an elongated cylindrical third tube extending further downstream directly from said second tube, said third tube having a bore in alignment and in fluid connection with the bore in said second tube, the outer diameter of said third tube being relatively smaller than the outer diameter of said second tube, said third tube terminating in a bulbous end portion, the bulbous end portion having outwardly extending bristles adhered thereto, the cavity of the threaded portion has a concentric spike extending in a proximal axial direction and adapted and constructed to penetrate a membrane of a reservoir containing a fluid material when said reservoir is affixed to said threaded portion.

2. A fluid applicator system comprising a proximal male threaded portion, said male threaded portion having a relatively large cavity, an elongated cylindrical first tube downstream from said male threaded portion and having a relatively smaller bore than said cavity in fluid connection with said cavity, an elongated cylindrical second tube extending further downstream directly from said first tube, said second tube having a bore in alignment and in fluid connection with the bore in said first tube, the outer diameter of said second tube being relatively smaller than the outer diameter of said first tube, an elongated cylindrical third tube extending further downstream directly from said second tube, said third tube having a bore in alignment and in fluid connection with the bore in said second tube, the outer diameter of said third tube being relatively smaller than the outer diameter of said second tube, said third tube terminating in a distal bulbous end portion, the bulbous end portion having outwardly extending bristles adhered thereto, the male threaded portion has screwed to it an inner female threaded hub, said hub having a reservoir the inside of which is in fluid connection with said cavity of said male threaded hub whereby to dispense fluid into said cavity and said bores of said first, second, and third tubes in series, the said reservoir is an elastic bulb that is collapsed when squeezed whereby the fluid applicator sucks up a quantity of liquid when said distal end is immersed in a source of liquid and said flexible bulb is released whereby it re-assumes a normal condition.

* * * * *